March 29, 1955 R. E. SHEPHERD Plant Pat. 1,373
ROSE PLANT
Filed May 18, 1954
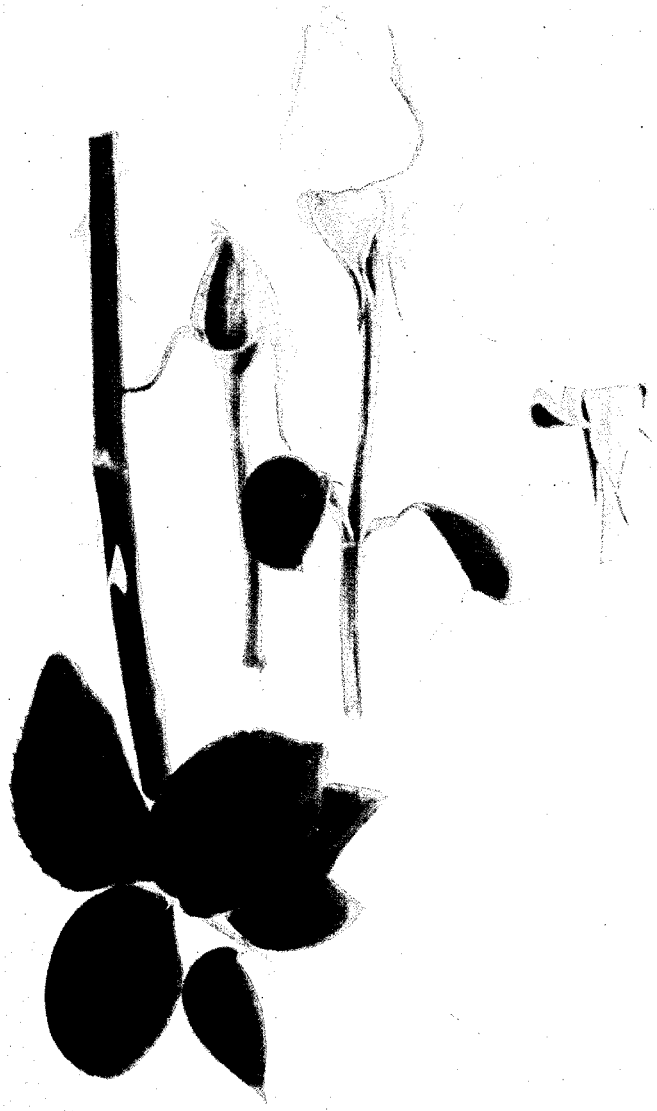
INVENTOR
Roy E. Shepherd
By Orville M. Kile
Plant Patent Agt.

United States Patent Office

Plant Pat. 1,373
Patented Mar. 29, 1955

1,373

ROSE PLANT

Roy E. Shepherd, Medina, Ohio, assignor to Edith C. Bosley, Mentor, Ohio

Application May 18, 1954, Serial No. 430,751

1 Claim. (Cl. 47—61)

My new variety originated from a cross between the varieties Peace (Plant Patent No. 591 and Fiesta (Plant Patent No. 389), made by me at my nurseries in Medina. It has been asexually reproduced by means of budding, by me in Medina and by nurserymen in Mentor, Ohio. The outstanding characteristics appear to be permanent.

My new variety resembles its parent "Peace" in its growth habits, being a very vigorous grower and very free-blooming, with foliage and bloom both unusually large.

Unlike either parent, my new variety produces blooms that are distinctly bi-color—this being its most outstanding feature.

Accompanying illustrations show four specimens of bud and flower in various stages of opening, together with separate portions of stem and of foliage.

In the following detailed description, color plate numbers refer to Ridgway's Color Standards and Nomenclature.

THE PLANT

Growth: Very vigorous; exceptionally strong for a hybrid tea rose plant.

Blooming habit: Very free bloomer.

Stem: Heavy; rigid; approximately Olive Green (Pl. IV), with generous tinges of dark red approximating Prussian Red (Pl. XXVII).

*Thorns.*—Large, numerous, downward - pointing; sharp; usually light green when stem is fresh—later may be dark red.

Foliage: Usually 3 to 5 leaflets.

*Leaflets*:

Size—Large, but specimens vary. Terminal leaflets are from 1½ to 2½ inches long and 1¼ to 1¾ inches wide.

Shape—Mature leaflets are broadly oval, with rounded base and apex, except for a very slight point at apex.

Color—Dark Green—Yew Green (Pl. XXXI) to Dark Dull Yellow Green (Pl. XXXII) on upper surface, and Jade Green (Pl. XXXI) on under surface, with sometimes a red tinge, particularly on the edges.

Texture—Heavy and leathery.

Aspect—Shiny. Center vein is very prominent and others insignificant, giving the effect of being definitely divided through the center.

Stipules—Long; clinging except for curved points.

Rachis—Heavy; deeply grooved above; studded with sharp spines below. Same green as foliage.

THE FLOWER

Bud:

*Shape.*—Pointed, with broad base.

*Size*—As calyx breaks, ¾ to 1 inch long above receptacle.

*Color.*—When color first shows, bud is approximately Spinel Red (Pl. XXVI). Just before beginning to unfurl, the color is approximately Lemon Chrome (Pl. IV), with each petal edged with Rose Doree (Pl. I).

*Peduncle.*—Short, averaging 2½ to 3 inches long. Strong, holding flower upright. Usually heavily tinged with dark red. Covered with many very small spines of reddish tinge.

Bloom:

*Size.*—Large, the first blooms in June measuring 5 to 6 inches across, ranging down to about 4 inches during the hot part of summer.

*Form.*—High-centered and full, retaining its shape although opening loosely in later stages, and finally becoming deep-cupped.

*Petalage.*—Approximately 30 petals.

*Color.*—The bloom is a distinct bi-color, the intensity of the colors varying greatly among specimens. Petals of a typical flower are Rose Doree (Pl I) on the face of the outer petals, with a base of Empire Yellow (Pl. IV) to Lemon Chrome (Pl. IV), while the inner petals are slightly lighter and have a face color from Eosine Pink to Begonia Rose (both Pl. I). The back of the petals is approximately Lemon Chrome (Pl. IV), later becoming approximately Apricot Yellow (Pl. IV).

Petals:

*Size.*—Approximately 2 by 2 inches. Inner petals much smaller.

*Shape.*—Outer petals approximately round and deeply cupped toward base. Edges undulate, giving slightly ruffled appearance. Edges also somewhat reflexed.

*Color.*—Shades of pink, with deep yellow aiglet.

*Texture.*—Substantial.

*Behavior.*—Cling well for a very long time, then drop cleanly.

*Longevity.*—Flower lasts well both on bush and as cut flower.

*Sepals.*—Mostly simple; broad at base; long-pointed.

*Fragrance.*—Tea fragrance, sometimes pronounced and sometimes lacking.

Reproductive organs:

*Pistils.*—Many, tightly bunched in center of flower, making a cushion.

Styles—Short; red-tinged.

Stigmas—Light yellow; small.

*Stamens.*—A great many; arise from a yellow pithy ring encircling the bunched pistils.

Filaments—Long; curved slightly inward, cupping around pistils; tinged with dark red to orange.

Anthers—Large; dark yellow, approximately Cadmium Yellow (Pl. III), turning light brown before flower fades.

Having thus disclosed my invention, I claim:

A new and distinct variety of hybrid tea rose plant substantially as herein shown and described, characterized particularly by its exceptionally strong growth; its free-blooming habit; its large, leathery foliage; and its very large, bi-color bloom of shades and tints of Begonia Rose on the inner surface of petals and of lemon to deep yellow on the outer surface.

No references cited.